US011534505B2

(12) United States Patent
Takahagi et al.

(10) Patent No.: US 11,534,505 B2
(45) Date of Patent: Dec. 27, 2022

(54) TRIARYL METHANE COMPOSITION, DYE COMPOSITION FOR OCULAR MEMBRANE DYEING

(71) Applicant: D. WESTERN THERAPEUTICS INSTITUTE, INC., Aichi (JP)

(72) Inventors: Makoto Takahagi, Hyogo (JP); Nobuhiro Haga, Hyogo (JP); Atsushi Inoue, Hyogo (JP)

(73) Assignee: D. WESTERN THERAPEUTICS INSTITUTE, INC., Nagoya (JP)

( * ) Notice: Subject to any disclaimer, the term of this patent is extended or adjusted under 35 U.S.C. 154(b) by 353 days.

(21) Appl. No.: 15/984,311

(22) Filed: May 18, 2018

(65) Prior Publication Data

US 2018/0264142 A1 Sep. 20, 2018

Related U.S. Application Data

(63) Continuation of application No. PCT/JP2016/081173, filed on Oct. 20, 2016.

(30) Foreign Application Priority Data

Nov. 27, 2020 (JP) ................. 2015-231303

(51) Int. Cl.
| | | |
|---|---|---|
| *A61K 49/00* | (2006.01) | |
| *C09B 11/12* | (2006.01) | |
| *A61K 31/13* | (2006.01) | |
| *A61K 31/136* | (2006.01) | |

(52) U.S. Cl.
CPC .......... *A61K 49/006* (2013.01); *A61K 31/136* (2013.01); *A61K 49/00* (2013.01); *C09B 11/12* (2013.01)

(58) Field of Classification Search
CPC ....... A61K 49/00; A61K 31/136; C09B 11/12
See application file for complete search history.

(56) References Cited

U.S. PATENT DOCUMENTS

| | | | |
|---|---|---|---|
| 5,198,558 A | 3/1993 | Rines et al. | |
| 6,057,160 A | 5/2000 | Silber et al. | |
| 7,731,941 B2 * | 6/2010 | Enaida | A61P 27/02 |
| | | | 424/10.32 |

FOREIGN PATENT DOCUMENTS

| | | |
|---|---|---|
| JP | 64031732 A | 2/1989 |
| JP | 4293966 A | 10/1992 |
| JP | 08094826 A | 4/1996 |
| JP | 08333517 A | 12/1996 |
| JP | 2008522953 A | 7/2008 |
| JP | 4200222 B2 | 12/2008 |
| WO | 2006062233 A1 | 6/2006 |

OTHER PUBLICATIONS

Nazim Mekaoui et al., Purification of Coomassie Brilliant Blue-G-250 by multiple dual mode countercuurent chromatography, Journal of Chromatography, vol. 1232, 134-141. (Year: 2012).*
John Daniel Stoops, Further stuides on the new Coomassie Brilliant Blue G-250 Protein Assay, Master Thesis (Year: 1978).*
Toshio Hisatomi et al. Staining Ability and Biocompatibility of Brilliant Blue G, Arch Ophthalmol, 124, 514-519. (Year: 2006).*
Hardy T.S. Kagimoto et al., Brilliant Blue G for ILM Staining and Peeling, Retina Today, 45-48. (Year: 2011).*
Mekaoui et al., "Purification of Coomassie Brilliant Blue G-250 by multiple dual mode countercurrent chromatography", Journal of Chromatography A 1232 (2012), pp. 134-141.
International Search Report and English translation for corresponding PCT Application PCT/JP2016/081173, dated Nov. 29, 2016.
International Preliminary Report on Patentability for corresponding PCT Application PCT/JP2016/081173, dated Jun. 7, 2018.

* cited by examiner

*Primary Examiner* — Michael G. Hartley
*Assistant Examiner* — Jagadishwar R Samala
(74) *Attorney, Agent, or Firm* — Myers Wolin, LLC

(57) ABSTRACT

A composition containing Brilliant Blue G (BBG) or a pharmaceutically acceptable salt thereof, and a positional isomer of Brilliant Blue G (BBG) or a pharmaceutically acceptable salt thereof, the composition containing 90 wt % or more and 100 wt % or less of one or both of Brilliant Blue G (BBG) and the pharmaceutically acceptable salt thereof in the total of the Brilliant Blue G (BBG), the pharmaceutically acceptable salt of Brilliant Blue G (BBG), the positional isomer of Brilliant Blue G (BBG), and the pharmaceutically acceptable salt of the positional isomer of Brilliant Blue G (BBG), a method for producing said composition, and a method of removing the ocular membrane of a human patient.

3 Claims, No Drawings

TRIARYL METHANE COMPOSITION, DYE COMPOSITION FOR OCULAR MEMBRANE DYEING

CROSS-REFERENCE TO RELATED APPLICATIONS

This application is a continuation under 35 USC 120 of International Application PCT/JP2016/081173, filed on Oct. 20, 2016, which claims priority from Japanese Patent Application 2015-231303, filed Nov. 27, 2015, the contents of each of which are incorporated herein by reference.

TECHNICAL FIELD

The present invention relates to high purity Brilliant Blue G (BBG), a method for producing the same, and a dye composition for ocular membrane dyeing having stable physical properties.

BACKGROUND ART

Japanese Patent No. 4200222 discloses a dye composition that is used for ocular membrane dyeing when removing the ocular membrane, and the composition contains Brilliant Blue G (BBG). This dyeing composition is also approved by the European Pharmaceutical Affairs and manufactured and sold as a medicine. This formulation has extremely excellent dyeing ability and has made a tremendous contribution to improvement of ophthalmic treatment. U.S. Pat. No. 6,057,160 discloses a method for producing BBG.

PRECEDING TECHNICAL DOCUMENT

Patent Document

Patent Document 1: Japanese Patent No. 4200222.
Patent Document 2: U.S. Pat. No. 6,057,160 specification.

SUMMARY

Technical Problem

In Japanese Patent No. 4200222, commercially available BBG or a sodium salt thereof is used. Physical properties of actual formulation may fluctuate.

Solution to Problem

As a result of studying the above problem, the present inventors have found that the commercially available BBG or a pharmaceutically acceptable salt thereof (hereinafter also simply referred to as "salt") contains BBG derivatives, and that BBG is only contained at most 50% to 60%. That is, when BBG is prepared and purified based on conventional synthetic methods, the BBG derivatives are contained therein, and BBG or the salt thereof is only contained at most 50% to 60%. The present inventors have found that the reason for fluctuation of the physical properties of the actual formulation is due to fluctuation of proportion of the BBG derivatives. The present inventors have found a method for producing BBG which greatly enhances content of BBG or the salt thereof. Basically, the present invention is based on the above findings.

That is, the first aspect of the present invention relates to triaryl methane composition containing a triaryl methane derivative or a pharmaceutically acceptable salt of the triaryl methane derivative. The triaryl methane derivative contains Brilliant Blue G (BBG) or a pharmaceutically acceptable salt of the Brilliant Blue G (BBG), and positional isomer of Brilliant Blue G (BBG) or a pharmaceutically acceptable salt of the positional isomer of Brilliant Blue G (BBG). From 90 wt % to 100 wt % of one or both of the Brilliant Blue G (BBG) and the pharmaceutically acceptable salt of Brilliant Blue G (BBG) is contained in total of "Brilliant Blue G (BBG), the pharmaceutically acceptable salt of Brilliant Blue G (BBG), the positional isomer of Brilliant Blue G (BBG), and the pharmaceutically acceptable salt of the positional isomer of Brilliant Blue G (BBG)". The "positional isomer of Brilliant Blue G (BBG)" means a compound which has a substituent to be added to a ring in Brilliant Blue G (BBG) at a different position. The above described composition may appropriately contain a carrier or a pharmaceutically acceptable solvent such as water or physiological saline.

That is, when explaining in more detail, the first aspect of the present invention relates to a triaryl methane composition, containing at least one of triaryl methane derivatives represented by formulas (1) to (3) and pharmaceutically acceptable salts of the triaryl methane derivatives represented by the formulas (1) to (3). From 90 wt % to 100 wt % of Brilliant Blue G (BBG) represented by the formula (1) or a pharmaceutically acceptable salt of the Brilliant Blue G (BBG) represented by the formula (1) is contained in the triaryl methane derivatives represented by the formulas (1) to (3) and the pharmaceutically acceptable salts of the triaryl methane derivatives represented by the formulas (1) to (3).

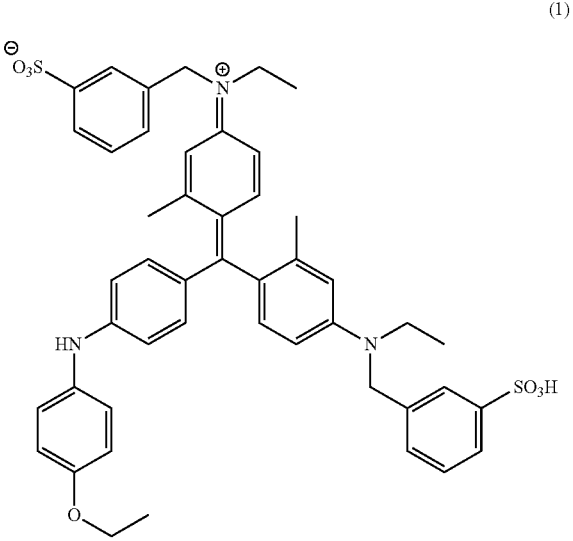

(1)

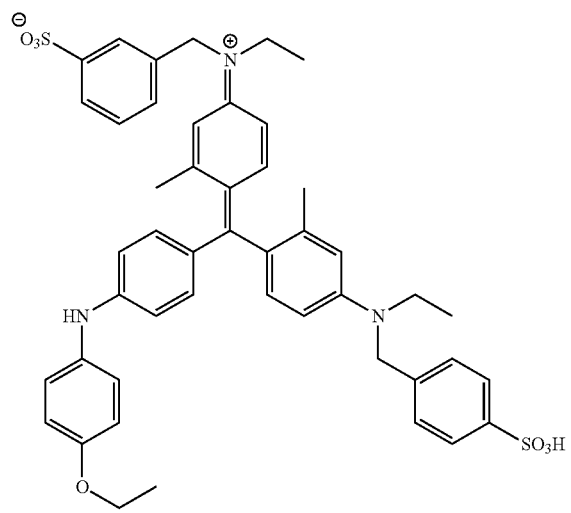

(2)

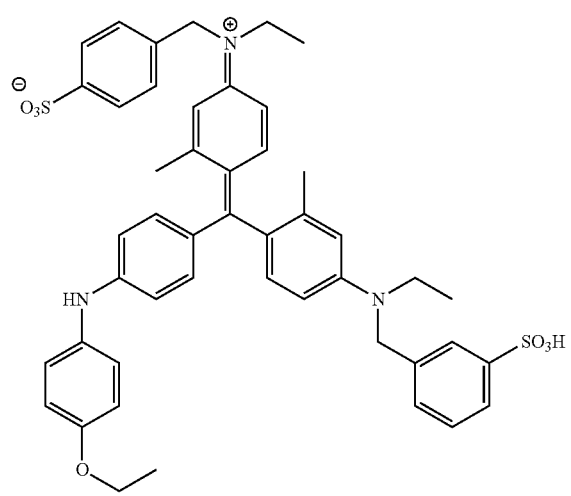

(3)

The above described composition is preferably used as a dyeing composition for ocular membrane dyeing at the time of removing the ocular membrane. That is, the dyeing composition for ocular membrane dyeing when removing the ocular membrane contains at least one of triaryl methane derivatives represented by formulas (1) to (3) and pharmaceutically acceptable salts of the triaryl methane derivatives represented by the formulas (1) to (3). From 90 wt % to 100 wt % of Brilliant Blue G (BBG) represented by the formula (1) or a pharmaceutically acceptable salt of the Brilliant Blue G (BBG) represented by the formula (1) is contained in the triaryl methane derivatives represented by the formulas (1) to (3) and the pharmaceutically acceptable salts of the triaryl methane derivatives represented by the formulas (1) to (3).

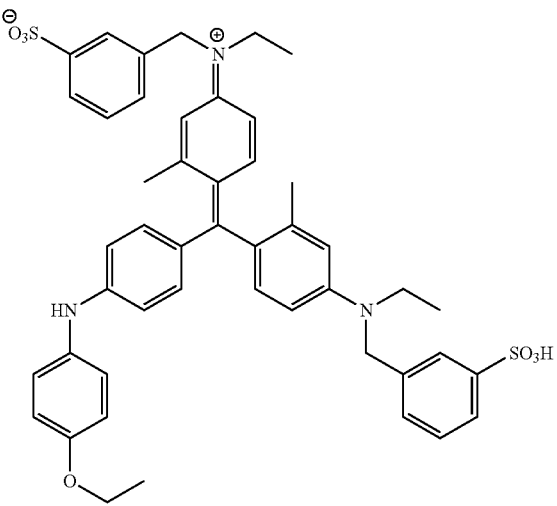

(1)

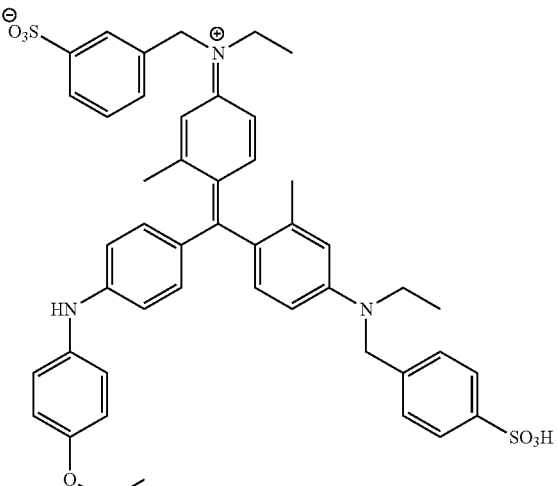

(2)

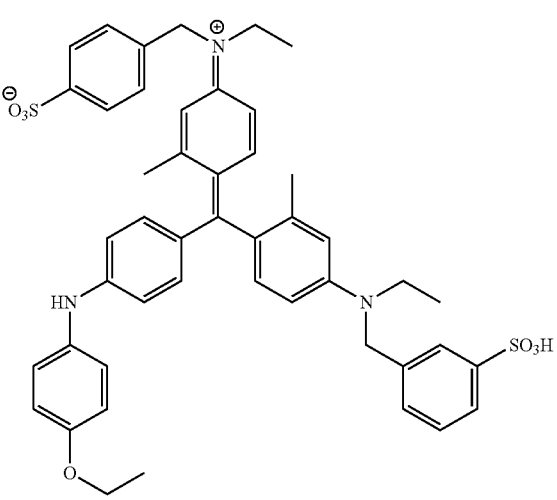

(3)

The second aspect of the present invention relates to a method for producing Brilliant Blue G (BBG) or a pharmaceutically acceptable salt of the Brilliant Blue G (BBG) capable of effectively removing positional isomer which has not been known to exist as described above. This method includes: a benzylation step of making ethyl-m-tolyl-amine represented by formula A1 react with a benzylation reagent, and thereby obtaining a compound represented by formula A2; a step of making sulfur trioxide or sulfuric acid act on the compound represented by the formula A2, and thereby obtaining benzyl ethyl-m-tolyl-amine derivative represented by formula A3; and
a step of obtaining Brilliant Blue G (BBG) represented by formula (1) or a pharmaceutically acceptable salt of the Brilliant Blue G (BBG) represented by the formula (1) from the benzyl ethyl-m-tolyl-amine derivative represented by the formula A3.

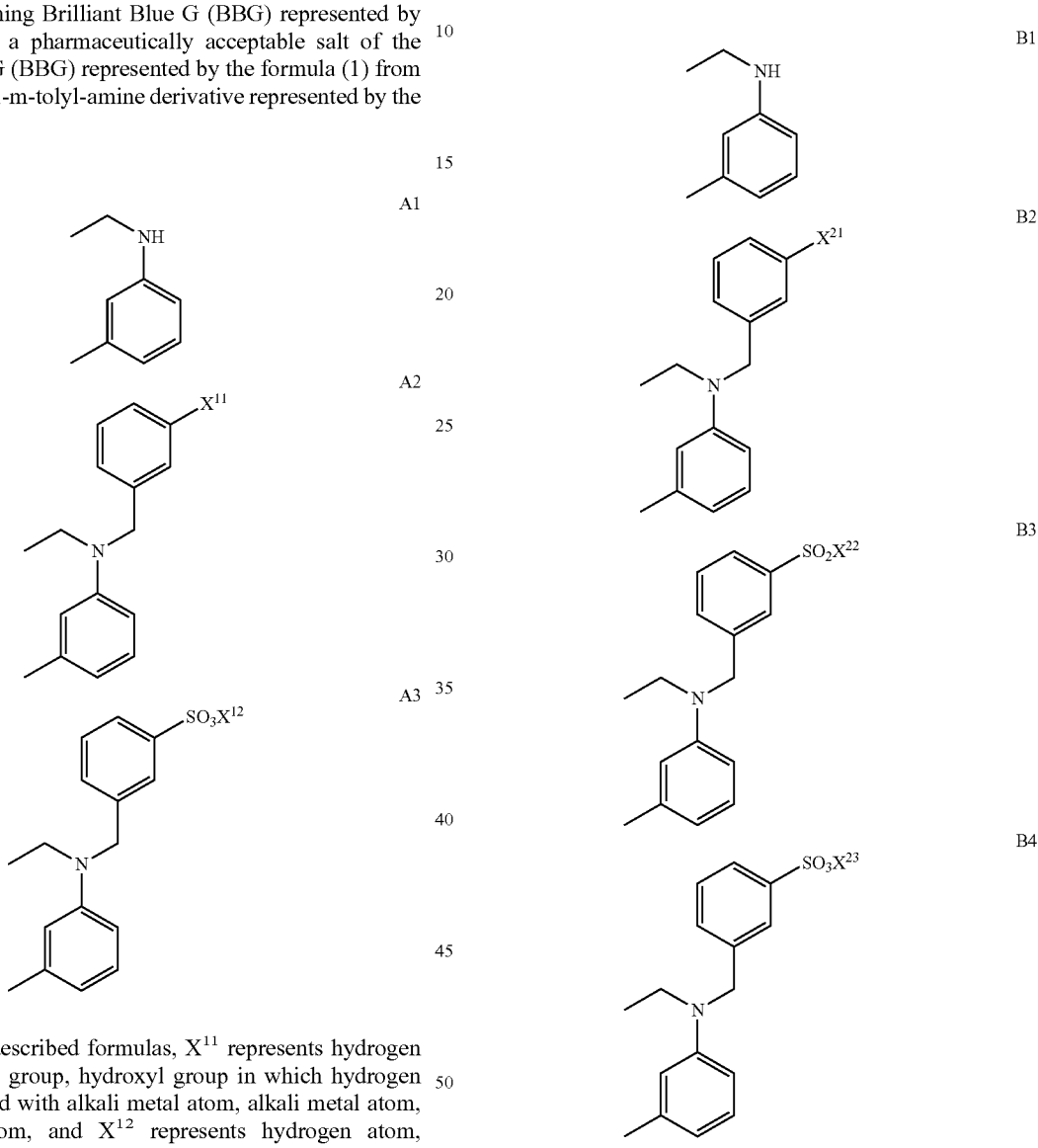

(In the above described formulas, $X^{11}$ represents hydrogen atom, hydroxyl group, hydroxyl group in which hydrogen atom is replaced with alkali metal atom, alkali metal atom, or halogen atom, and $X^{12}$ represents hydrogen atom, hydroxyl group, hydroxyl group in which hydrogen atom is replaced with alkali metal atom, alkali metal atom, or halogen atom.)

Another embodiment of the second aspect of the present invention relates to a method for producing Brilliant Blue G (BBG) or a pharmaceutically acceptable salt of the Brilliant Blue G (BBG), including: a step of making ethyl-m-tolyl-amine represented by formula B1 react with a benzylation reagent to which halogen atom is added, and thereby obtaining a halogenated compound represented by formula B2; a step of replacing halogen atom of the halogenated compound represented by the formula B2, and thereby obtaining benzyl ethyl-m-tolyl-amine derivative represented by formula B3; a step of making benzyl ethyl-m-tolyl-amine derivative represented by the formula B3 and alkali react with each other, and thereby obtaining a benzyl ethyl-m-tolyl-amine derivative represented by formula B4; and a step of obtaining Brilliant Blue G (BBG) represented by formula (1) or a pharmaceutically acceptable salt of the Brilliant Blue G (BBG) represented by the formula (1) from the benzyl ethyl-m-tolyl-amine derivative represented by the formula B4.

(In the above described formulas, $X^{21}$ represents halogen atom, $X^{22}$ represents halogen atom, and $X^{23}$ represents hydrogen atom, hydroxyl group, hydroxyl group in which hydrogen atom is replaced with alkali metal atom, alkali metal atom, or halogen atom.)

In this method, the step of replacing halogen atom of the halogenated compound represented by the formula B2, and thereby obtaining benzyl ethyl-m-tolyl-amine derivative represented by the formula B3 preferably includes: a step of making sulfide act on the halogenated compound represented by the formula B2, and thereby obtaining compound represented by formula B2-1; and a step of making electrophilic reagent $SO_2Cl_2$ act on the compound represented by the formula B2-1, and thereby obtaining benzyl ethyl-m-tolyl-amine derivative represented by the formula B3 and having chlorine atom as $X^{21}$.

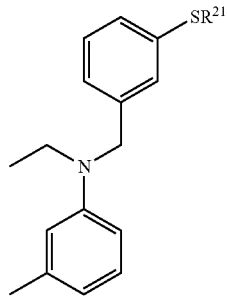

(B2-1)

(In the above described formula, $R^{21}$ represents phenyl group or benzyl group, methyl group, ethyl group, hydroxyl group, or phenyl group or benzyl group which may be replaced with halogen atom.)

In this method, the step of replacing halogen atom of the halogenated compound represented by the formula B2, and thereby obtaining benzyl ethyl-m-tolyl-amine derivative represented by the formula B3 is preferably a step of making Grignard reagent act on the halogenated compound represented by the formula B2, making $SO_2$ act thereon, and then making halogen ion act thereon, and thereby obtaining benzyl ethyl-m-tolyl-amine derivative represented by the formula B3.

Advantageous Effect of Invention

According to the present invention, a triaryl methane composition can be provided. The triaryl methane composition is high in BBG or a pharmaceutically acceptable salt of BBG, and consequently physical properties thereof do not fluctuate easily.

According to the present invention, a dye composition for ocular membrane dyeing when removing the ocular membrane can be provided. The dye composition is high in BBG or a pharmaceutically acceptable salt of BBG, and physical properties thereof do not fluctuate easily.

According to the present invention, a method for producing BBG, which is high in BBG or a pharmaceutically acceptable salt of BBG, can be provided.

DESCRIPTION OF EMBODIMENTS

Hereinafter, embodiments of the present invention will be described. The present invention is not limited to the embodiments described below, but includes modifications appropriately modified from the following embodiments within a scope obvious to those skilled in the art.

Triaryl Methane Composition

A triaryl methane composition of the present invention contains at least one of triaryl methane derivatives represented by formulas (1) to (3) and pharmaceutically acceptable salts thereof.

Among the triaryl methane derivatives represented by the formulas (1) to (3), the triaryl methane derivative represented by the formula (1) is Brilliant Blue G (BBG). The triaryl methane derivatives represented by the formulas (2) and (3) are compounds which have been contained much in BBG when producing BBG and which have not been distinguished from BBG. These compounds are isomers of BBG, and each of the compounds has molecular weight same as that of BBG. Therefore, it is considered that these isomers have not been separated even when purifying the synthesized BBG. Further, it is difficult to extract only BBG from a triaryl methane composition in which these isomers are mixed. In the present invention, from 90 wt % to 100 wt % of Brilliant Blue G (BBG) represented by the formula (1) or a pharmaceutically acceptable salt thereof is contained in the triaryl methane derivatives represented by the formulas (1) to (3) and the pharmaceutically acceptable salts of the triaryl methane derivatives represented by the formulas (1) to (3).

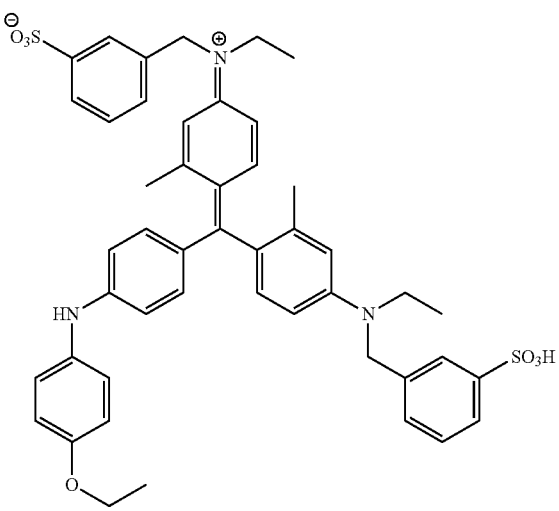

(1)

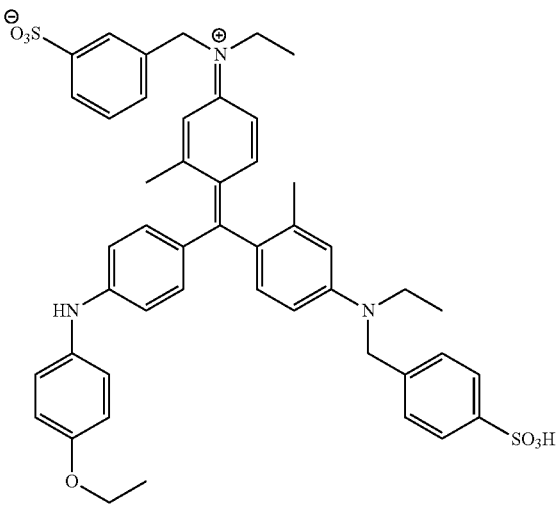

(2)

-continued (3)

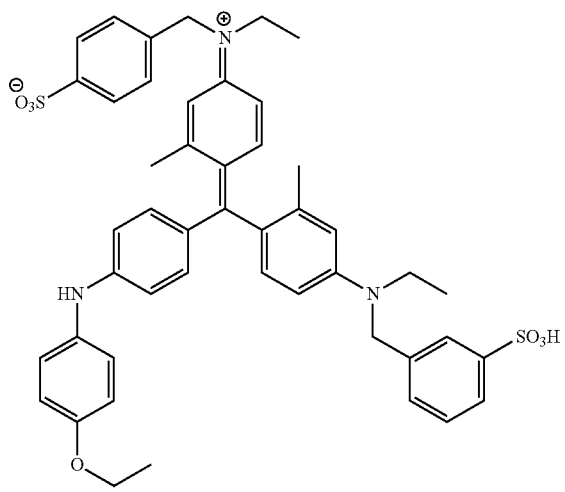

The above described formulas (1) to (3) represent triaryl methane derivatives represented by the formulas (1) to (3) in a state of being ionized in, for example, an aqueous solution. The present invention may contain triaryl methane derivatives represented by the formulas (1) to (3) in a state of not being ionized. The compound represented by the formula (1) is Brilliant Blue G (BBG), and BBG is also called N-ethyl-N-[4-[[4-[N-ethyl-N-(3-sodiosulfobenzyl)amino]-2-methylphenyl][4-[(4-ethoxyphenyl)amino]phenyl]methylene]-3-methyl-2,5-cyclohexadien-1-ylidene]-3]sulfonatobenzenemethanaminium. The compounds represented by the formulas (2) and (3) are positional isomers of BBG.

This composition preferably contains from 90 wt % to 99.99 wt % of Brilliant Blue G (BBG) represented by the formula (1) or the pharmaceutically acceptable salt thereof in the triaryl methane derivatives represented by the formulas (1) to (3) or the pharmaceutically acceptable salts thereof. The range may be 90 wt % or more and 99.9 wt % or less, 90 wt % or more and 99 wt % or less, 90 wt % or more and 98 wt % or less, 90 wt % or more and 97 wt % or less, 90 wt % or more and 95 wt % or less,
91 wt % or more and 99.99 wt % or less, 91 wt % or more and 99.9 wt % or less, 91 wt % or more and 99 wt % or less, 91 wt % or more and 98 wt % or less, 91 wt % or more and 97 wt % or less, 91 wt % or more and 95 wt % or less,
92 wt % or more and 99.99 wt % or less, 92 wt % or more and 99.9 wt % or less, 92 wt % or more and 99 wt % or less, 92 wt % or more and 98 wt % or less, 92 wt % or more and 97 wt % or less, 92 wt % or more and 95 wt % or less,
93 wt % or more and 99.99 wt % or less, 93 wt % or more and 99.9 wt % or less, 93 wt % or more and 99 wt % or less, 93 wt % or more and 98 wt % or less, 93 wt % or more and 97 wt % or less, 93 wt % or more and 95 wt % or less,
95 wt % or more and 99.99 wt % or less, 95 wt % or more and 99.9 wt % or less, 95 wt % or more and 99 wt % or less, 95 wt % or more and 98 wt % or less, or 95 wt % or more and 97 wt % or less.

Brilliant Blue G (BBG) represented by the formula (1) or the pharmaceutically acceptable salt thereof is ionized in, for example, aqueous solution, and there exists Brilliant Blue G (BBG) not represented by the formula (1) or a pharmaceutically acceptable salt thereof. However, those forms are obvious for a person skilled in the art, and are naturally included in Brilliant Blue G (BBG) represented by the formula (1) or the pharmaceutically acceptable salt thereof regardless of being ionized or not. In addition, BBG or a salt thereof may be a solvate (for example, a hydrate). Since such a form substantially behaves in the same manner as BBG or the salt thereof in aqueous solution, the form is included in Brilliant Blue G (BBG) represented by the formula (1) or the pharmaceutically acceptable salt thereof.

Examples of pharmacologically acceptable salts include salts formed with inorganic bases, ammonia, organic bases, inorganic acids, organic acids, basic organic acids, halogen ions and the like, and internal salts. Examples of inorganic bases include alkali metals (Na, K etc.) and alkaline earth metals (Ca, Mg etc.). Examples of organic bases include trimethylamine, triethylamine, choline, procaine, ethanolamine, and the like. Examples of inorganic acids include hydrochloric, hydrobromic, sulfuric, nitric, phosphoric acid, and the like. Examples of organic acids include p-toluenesulfonic acid, methanesulfonic acid, formic acid, trifluoroacetic acid, maleic acid, and the like. Examples of basic amino acids include lysine, arginine, ornithine, histidine, and the like.

Dyeing Composition for ocular membrane dyeing when removing the ocular membrane

The triaryl methane composition can be used as an active constituent of a dyeing composition for ocular membrane dyeing when removing the ocular membrane. That is, as disclosed in Patent document 1, BBG or a salt thereof is effective as the active constituent (dye) of the dyeing composition for the ocular membrane dyeing when removing the ocular membrane.

According to one preferred embodiment of the present invention, the dyeing composition can be used as a surgical adjuvant in an ophthalmic operation of eyeball disease such as macular hole, retinal detachment due to high myopic (hymyopic) macular hole, epiretinal membrane, proliferative diabetic retinopathy, diabetic macular edema, proliferative vitreoretinopathy, vitreoretinal diseases including specific cataract such as overripe cataract and congenital cataract, partial thickness keratoplasty, and the like. According to the dyeing composition of the present invention, it is possible to confirm more clearly the ocular membrane which is difficult to identify, and it is possible to improve safety during surgical operations.

In more preferable embodiment of the present invention, the dyeing composition can be used, more preferably, for dyeing of an inner limiting membrane or an anterior capsule.

According to one embodiment of the present invention, the dyeing composition of the present invention can be used in combination with a pharmacologically acceptable carrier. It is possible to formulate as a set together with a solution and drug powder, a form of solution filled in a syringe, or gel-like solution in combination with hyaluronic acid. Most preferably, it is formulated as a solution, but it is not necessarily limited thereto.

According to one embodiment of the present invention, the dyeing composition is formulated as a pharmaceutically acceptable solution, but it is not necessarily limited thereto. This is due to the characteristic of BBG that it is directly and easily dissolved in an intraocular wash and it can be sterilized by a syringe filter.

In addition, according to one embodiment of the present invention, the dyeing composition can be formulated as a solution containing the dyeing composition dissolved in an intraocular infusion solution, a balanced salt solution (BSS), physiological saline solution, or most preferably, OPE-GUARD-MA (Senju Pharmaceutical Co., Ltd., Osaka, Japan) which is the intraocular infusion solution (intraocular wash). It is, however, not necessarily limited thereto.

Further, according to one embodiment of the dyeing composition of the present invention, it is preferable that an osmotic pressure is around 298 mOsm. According to this embodiment, the dyeing composition has the same osmotic pressure as that of physiological saline solution. Previously, it has been reported that damage of retinal pigment epithelium by ICG may be derived from hypotonicity of the solution. In this context, the dyeing composition of one embodiment of the present invention has an excellent effect that it does not cause tissue damage (cell dropout or cell death, etc.) related to cell swelling or dehydration, such as damage caused by difference in osmotic pressure in the retinal pigment epithelium.

In one preferred embodiment of the present invention, it is preferable that the dyeing composition of the present invention has a neutral pH, namely pH around pH=7.4.

In relation to the agent of this aspect, there is provided a method including administering the agent to the eye of a patient, dyeing an ocular membrane, and removing the dyed ocular membrane. This method includes a step of producing the dye composition containing BBG or a salt thereof, a step of dyeing the ocular membrane by using the dyeing composition having predefined concentration, and a step of removing the dyed ocular membrane. That is, the agent of this aspect can be used as a surgical adjuvant for ophthalmic operation. As one preferred embodiment of the present invention, the ophthalmic operation is operated for eye balls of mammals, and more preferably for human eye balls.

In addition, in one embodiment of the present invention, the dyeing composition and/or a dyeing method by using the same can be appropriately used as a part of ophthalmic operation. According to a preferred embodiment of the present invention, the foregoing operations for ophthalmic diseases are surgical operations to treat macular hole, retinal detachment due to myopic macular hole, epiretinal membrane, proliferative diabetic retinopathy, diabetic macular edema, proliferative vitreoretinopathy, specific cataract such as overripe cataract and congenital cataract, partial thickness keratoplasty, and the like, and most preferably to treat vitreoretinal diseases (in particular, macular hole and epiretinal membrane (FRMS)) and cataract.

In relation to the agent of this aspect, usage of BBG or a salt thereof to manufacture a dyeing composition for treatment of ophthalmic diseases can be provided. In particular, the present invention can also provide usage of BBG or the salt thereof to manufacture a dyeing composition for removing ocular membrane.

Next, a dosage of BBG in the agent of the present invention will be described. The agent of the present invention contains BBG at concentration of 0.1 to 10 mg/ml, preferably of 0.1 to 1.0 mg/ml, most preferably of 0.1 to 0.25 mg/ml. Dyeing effect can be obtained adequately by BBG contained in the dyeing composition at low concentration of 0.25 mg/ml.

The form of the agent of the present invention is not particularly limited. An exemplary form is an injection. In addition, by making the agent of the present invention in the form disclosed in the above described Patent document, it is possible to locally administer the agent within the eye. For producing the injection, a known carrier (water etc.) and an active constituent are mixed and filled in a syringe. A known method can be appropriately used as a method for manufacturing the form of the agent.

A neuroprotective agent of the present invention may be orally administered. In this case, it can be formulated by mixing a known carrier and BBG or a salt thereof as an active agent and tableting with a tableting machine.

In a case of using the agent of the present invention as a dyeing composition, appropriate amount of the dyeing composition may be administered to a treatment region. For example, 1 cc or more and 1 ml or less of the agent of the present invention in the form of injection may be administered. In a case of using the agent of the present invention as the neuroprotective agent or an anti-inflammatory agent, it may be administered, for example, once to three times per day for a predetermined period of time.

Method for producing BBG or a salt thereof (basic synthesizing scheme)

Next, a method for producing BBG and a salt thereof will be described. This basic method for producing BBG and the salt thereof includes the following three steps. Another step may be included before or after each of these steps.

Make ethyl-m-tolyl-amine represented by formula A1 react with a benzylation reagent, and obtain a compound represented by formula A2 (benzylation step).

Make sulfur trioxide or sulfuric acid act on the compound represented by the formula A2, and obtain benzyl ethyl-m-tolyl-amine derivative represented by formula A3.

Obtain Brilliant Blue G (BBG) represented by formula (1) or a pharmaceutically acceptable salt thereof from the benzyl ethyl-m-tolyl-amine derivative represented by the formula A3.

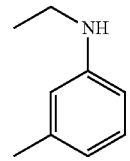

A1

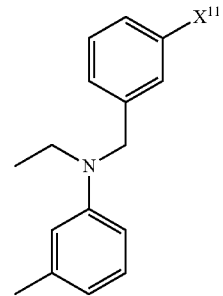

A2

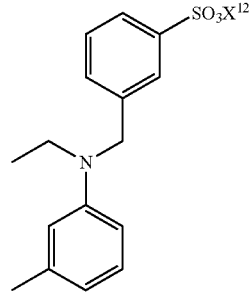

A3

In the above described formulas, $X^{11}$ represents hydrogen atom, hydroxyl group, hydroxyl group in which hydrogen atom is replaced with alkali metal atom, alkali metal atom, or halogen atom. Preferable example of $X^{11}$ is the hydrogen atom. The hydroxyl group in which hydrogen atom is replaced with alkali metal atom means a group in which hydrogen atom of hydroxyl group is replace with alkali metal, for example, like —ONa. Examples of the alkali metal are Na and K. Examples of the halogen atom are F, Cl, Br, and I.

In the above described formulas, $X^{12}$ represents hydrogen atom, hydroxyl group, hydroxyl group in which hydrogen atom is replaced with alkali metal atom, alkali metal atom, or halogen atom. Preferred example of $X^{12}$ is the hydrogen atom or sodium atom.

Step of Making Ethyl-m-Tolyl Amine Represented by the Formula A1 React with a Benzylation Reagent, and Thereby Obtaining a Compound Represented by the Formula A2

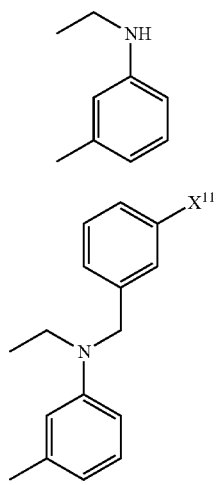

In this step, for example, a compound represented by A1 is added to an alkaline organic solvent under a rare gas atmosphere, and a benzylation reagent to which a halogen atom is added is dropped while stirring to maintain the stirring state. An example of the rare gas is argon. Examples of the organic solvents are polar solvents such as acetonitrile. An example of an alkalizing agent is potassium carbonate. The reaction may be carried out at 10° C. or more and 35° C. or less (for example, at room temperature). An example of stirring time is 1 hour or more and 1 day or less. The reaction is usually carried out under atmospheric pressure.

For example, the alkalizing agent may be used in an amount equal to or greater than a half of the molar number of the compound represented by A1 and equal to or less than 2 times of the molar number of the compound represented by A1. The benzylation reagent to which a halogen atom is added means a compound in which a hydrogen atom is replaced with a halogen atom in the benzylation reagent. Examples of the benzylation reagent to which a halogen atom is added are benzyl bromide, benzyl chloride, and benzyl fluoride. For example, the benzylation reagent to which a halogen atom is added may be used in an amount equal to or greater than a half of the molar number of the compound represented by A1 and equal to or less than 2 times of the molar number of the compound represented by A1.

Step of Making Sulfur Trioxide or Sulfuric Acid Act on the Compound Represented by the Formula A2, and Thereby Obtaining Benzyl Ethyl-m-Tolyl-Amine Derivative Represented by Formula A3

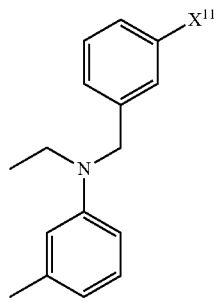

This step is a step of making sulfur trioxide or sulfuric acid act on the compound obtained by the previous step and represented by the formula A2, for example, under ice-cooling, and thereby obtaining benzyl ethyl-m-tolyl-amine derivative represented by the formula A3. Fuming sulfuric acid may be used as the sulfur trioxide. More specifically, the compound represented by A2 is diluted with concentrated sulfuric acid under ice-cooling. Thereafter, the fuming sulfuric acid is dropped over time under ice-cooling. Then, stirring is carried out at room temperature or in a hot water bath (for example, 100° C.) to allow the reaction to proceed. An example of the dropping time is not less than 5 minutes and not more than 1 hour. An example of the stirring time is not less than 2 hours and not more than 1 day.

After stirring, it is possible to obtain a salt of the compound represented by A3 (for example, $X^{12}$ is sodium), by appropriately dropping an alkali (for example, sodium hydroxide or sodium hydrogen carbonate) with stirring and by appropriately drying.

In this step, it is preferable to increase the purity and reduce the content of isomer by cesium salification of the compound represented by A3. In order to perform the cesium salification of the compound represented by A3, for example, the compound represented by the formula A3 may be reacted with a cesium compound (for example, cesium carbonate).

Step of Obtaining Brilliant Blue G (BBG) Represented by Formula (1) or a Pharmaceutically Acceptable Salt Thereof from the Benzyl Ethyl-m-Tolyl-Amine Derivative Represented by the Formula A3

In order to obtain BBG or a salt thereof from the compound represented by the formula A3, for example, the following steps may be carried out.

First, two compounds represented by the formula A3 are bonded via a compound represented by the following formula A3-1.

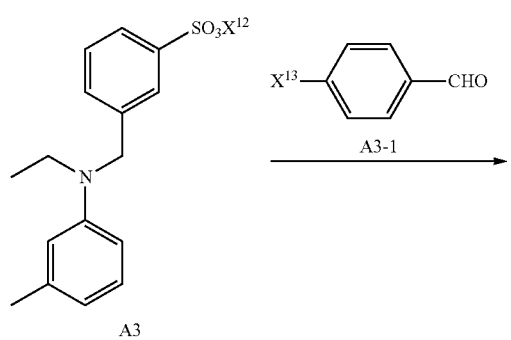

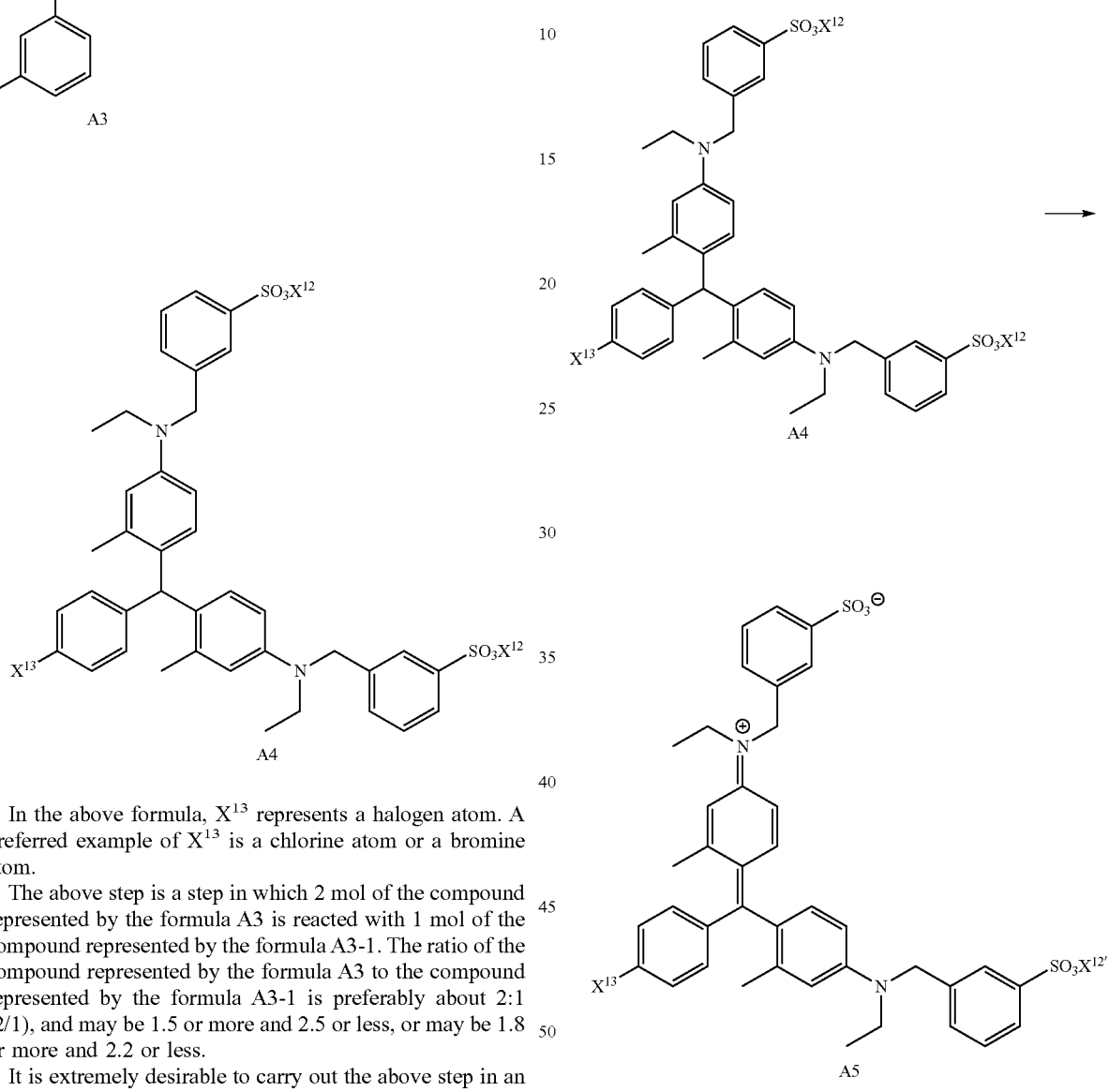

In the above formula, $X^{13}$ represents a halogen atom. A preferred example of $X^{13}$ is a chlorine atom or a bromine atom.

The above step is a step in which 2 mol of the compound represented by the formula A3 is reacted with 1 mol of the compound represented by the formula A3-1. The ratio of the compound represented by the formula A3 to the compound represented by the formula A3-1 is preferably about 2:1 (2/1), and may be 1.5 or more and 2.5 or less, or may be 1.8 or more and 2.2 or less.

It is extremely desirable to carry out the above step in an alcohol solvent. Examples of alcohol are methanol, ethanol and butanol, and the preferred alcohol is (diluted) ethanol. In this step, it is desirable to carry out the reaction under the condition that the solution is made acidic (for example, pH 0.3 or more and 1 or less) by using an acidifying agent. Examples of the acidifying agent are hydrochloric acid, concentrated hydrochloric acid, concentrated sulfuric acid, and concentrated nitric acid. Among these examples, hydrochloric acid or concentrated hydrochloric acid is preferable. It is preferable to perform stirring for 10 hours or more and 200 hours or less under a condition of 100° C. or more and 140° C. or less, after dropping the compound represented by the formula A3-1. After returning the reaction solution to 15° C. or more and 35° C. or less (for example, room temperature), alkali is added. An example of alkali is sodium hydroxide aqueous solution. Alkaline is added, and pH is adjusted to be 0.5 or more and 1.5 or less. By purifying the obtained precipitate, crystals represented by formula A4 can be obtained.

Next, a compound represented by formula A5 having high reactivity is obtained from the compound represented by the formula A4.

In the above formulas, $X^{12'}$ represents an alkali metal atom. A preferred example of $X^{12'}$ is a potassium atom or a sodium atom.

In this step, an acidic polar solvent is used to cause an oxidizing agent to act on the compound represented by the formula A4. An example of the polar solvent is a mixed solvent of acetonitrile and water. An example of acidity of the solvent is pH 1.5 or more and 3 or less. An example of the oxidizing agent is CAN. In this step, conditions may be appropriately adjusted with reference to examples described later.

Next, para-phenetidine is allowed to act on a compound represented by formula A5 to obtain BBG represented by formula A6.

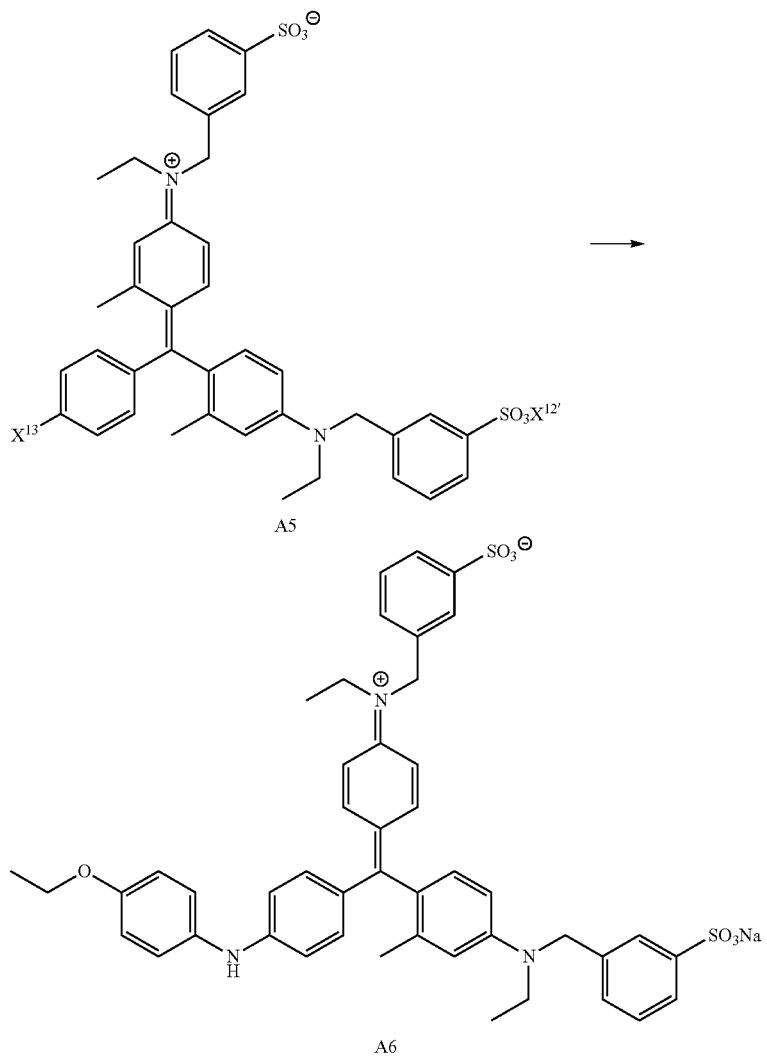

Since the compound represented by the formula A5 and para-phenetidine react with 1:1, the ratio of the compound represented by the formula A5 to para-phenetidine needs to be about 1 (1/1), and may be 0.8 or more and 1.2 or less, or may be 0.9 or more and 1.1 or less.

BBG or a salt thereof obtained in this way is appropriately purified, and thereby make it possible to obtain BBG or the salt thereof having a low mixing ratio of isomers.

Method for Producing BBG or a Salt Thereof (Plan C-1 and C-2)

Next, another example different from the above for producing BBG or a salt thereof well be explained. This method includes:

a step of making ethyl-m-tolyl-amine represented by formula B1 react with a benzylation reagent to which a halogen atom is added, and thereby obtaining a halogenated compound represented by formula B2;

a step of replacing the halogen atom of the halogenated compound represented by the formula B2, and thereby obtaining benzyl ethyl-m-tolyl-amine derivative represented by formula B3;

a step of making benzyl ethyl-m-tolyl-amine derivative represented by the formula B3 and alkali react with each other, and thereby obtaining a benzyl ethyl-m-tolyl-amine derivative represented by formula B4; and a step of obtaining Brilliant Blue G (BBG) represented by formula 1 or a pharmaceutically acceptable salt thereof from the benzyl ethyl-m-tolyl-amine derivative represented by the formula B4.

The step of obtaining Brilliant Blue G (BBG) represented by formula 1 or a pharmaceutically acceptable salt thereof from the benzyl ethyl-m-tolyl-amine derivative represented by the formula B4 is similar to the step of obtaining Brilliant Blue G (BBG) represented by formula 1 or a pharmaceutically acceptable salt thereof from the compound previously explained and represented by the formula A3.

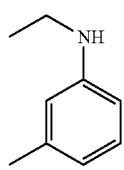

B1

-continued

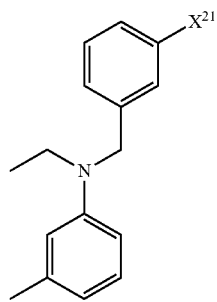

B2

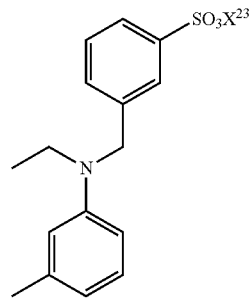

B3

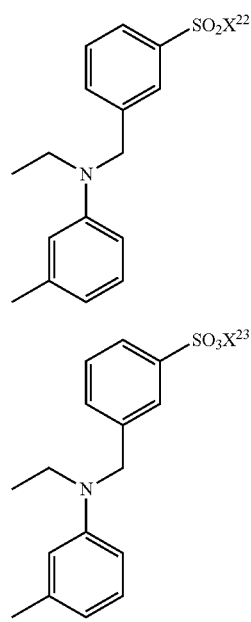

B4

In the above described formulas, $X^{21}$ represents a halogen atom. A preferred example of $X^{21}$ is a chlorine atom or a bromine atom, and the bromine atom is preferable.

$X^{22}$ represents a halogen atom. A preferred example of $X^{22}$ is a chlorine atom or a bromine atom, and the chlorine atom is preferable.

$X^{23}$ represents a hydrogen atom, a hydroxyl group, a hydroxyl group in which a hydrogen atom is replaced with an alkali metal atom, an alkali metal atom, or a halogen atom. A preferred example of $X^{23}$ is the hydrogen atom or a sodium salt.

Step of Making Ethyl-m-Tolyl-Amine Represented by the Formula B1 React with the Benzylation Reagent to which a Halogen Atom is Added, and Thereby Obtaining the Halogenated Compound Represented by the Formula B2

A specific example of this step is disclosed in Example 2. An example of the benzylation reagent to which a halogen atom is added is a compound represented by $X^{21}$-Ph-$CH_2$—$X^{211}$. The group $X^{21}$— is preferably present at a meta position of the group —$CH_2$—$X^{211}$. Ph means a benzene ring. $X^{21}$ is the same as that defined above, $X^{211}$ may be the same as or different from $X^{21}$, and $X^{211}$ represents a halogen atom. Since the compound represented by the formula B1 (which is the same as the compound represented by the formula A1) and the benzylation reagent to which a halogen atom is added react with 1:1, the ratio of the compound represented by the formula B1 to the benzylation reagent to which a halogen atom is added needs to be about 1 (1/1), and may be 0.8 or more and 1.2 or less, or may be 0.9 or more and 1.1 or less.

Step of Replacing the Halogen Atom of the Halogenated Compound Represented by the Formula B2, and Thereby Obtaining the Benzyl Ethyl-m-Tolyl-Amine Derivative Represented by the Formula B3

In this step, two systems can be mainly adopted as described below. One system includes:
a step of making sulfide act on the halogenated compound represented by the formula B2, and thereby obtaining a compound represented by a formula B2-1; and
a step of making electrophilic reagent $SO_2Cl_2$ act on the compound represented by the formula B2-1, and thereby obtaining benzyl ethyl-m-tolyl-amine derivative represented by the formula B3 and having chlorine atom as $X^{21}$.

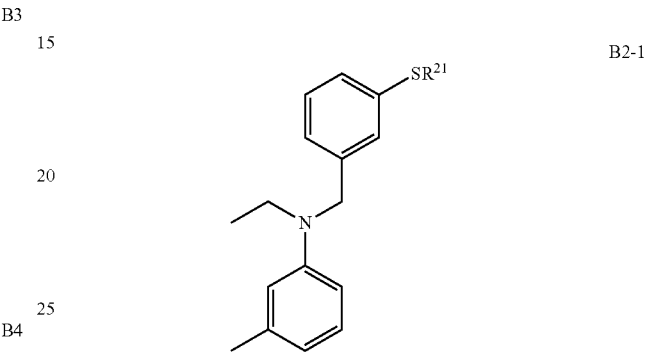

B2-1

In the above described formulas, $R^{21}$ represents phenyl group or benzyl group, methyl group, ethyl group, hydroxyl group, or phenyl group or benzyl group which may be replaced with a halogen atom. A preferred example of $R^{21}$ is a benzyl group.

In the step of making sulfide act on the halogenated compound represented by the formula B2 and thereby obtaining a compound represented by the formula B2-1, an example of the sulfide is a compound represented by a formula $HSR^{21}$. This step may be performed in the presence of a base.

The step of making electrophilic reagent $SO_2Cl_2$ act on the compound represented by the formula B2-1, and thereby obtaining benzyl ethyl-m-tolyl-amine derivative represented by the formula B3 and having chlorine atom as $X^{21}$ may be performed in the presence of an acid.

The other system of the step of replacing the halogen atom of the halogenated compound represented by the formula B2 and thereby obtaining the benzyl ethyl-m-tolyl-amine derivative represented by the formula B3 is a step of making Grignard reagent act on the halogenated compound represented by the formula B2, making $SO_2$ act thereon, and then making halogen ion act thereon, and thereby obtaining benzyl ethyl-m-tolyl-amine derivative represented by the formula B3. The halogen ion is, for example, a chloride ion derived from N-chlorosuccinimide. This step is described in Example 3, and may be appropriately adjusted based on Example 3.

Step of Making Benzyl Ethyl-m-Tolyl-Amine Derivative Represented by the Formula B3 and Alkali React with Each Other, and Thereby Obtaining the Benzyl Ethyl-m-Tolyl-Amine Derivative Represented by the Formula B4

Alkali is, for example, a compound represented by $HOX^{23}$. A specific example of the alkali is sodium hydroxide.

Example 1

Synthesis of the Compound Represented by the Formula A2 from the Compound Represented by the Formula A1 (IntBBG-02 from IntBBG-01)

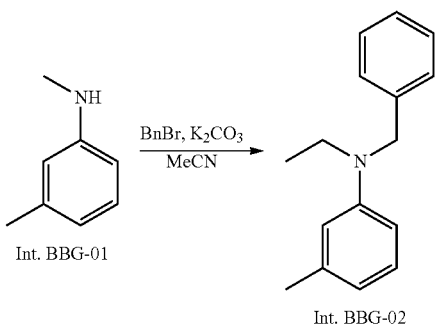

Int. BBG-01

Int. BBG-02

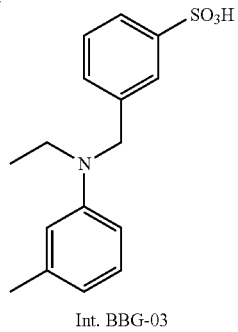

Int. BBG-03

Under an argon stream, Int BBG-01: 76.1 grams (0.5629 mol, TC1), $K_2CO_3$: 116.7 grams (0.8443 mmol), acetonitrile (MeCN): 560 ml were charged to 2 L Kolben, benzyl bromide (BnBr) (TC1): 105.9 g (0.6191 mol) was added at 18° C. (no heated), and stirring was carried out for four hours at room temperature (heat of reaction was gradually generated and raised to internal temperature: 28° C.)

After confirming the reaction by HPLC, insoluble matter was filtered off and the filtrate was concentrated under reduced pressure (bath temperature: 35 to 45° C.). AcOEt: 1.2 L, water: 400 mL were added to the obtained concentrated residue and extracted. After washing the obtained organic layer with brine: 200 mL, dried with $Na_2SO_4$, and concentrated under reduced pressure (bath temperature: 35 to 45° C.).

The obtained residue (138.2 g) was purified by silica gel column chromatography (N60 silica gel 1.1 kg, $CHCl_3$/Hep=1/2 to 1/10), and a crude material of BBG-02: 125.7 g (pale yellow oil, 99.1% yield, LC 86.7%) was obtained.

The obtained crude material: 125.7 g was subjected to vacuum distillation purification, and Int.BBG-02: 90.05 g {pale yellow oil, 71.0% yield, LC 98.5%, lot. 1403311, bp. 141.5 to 154° C. (0.13 to 0.15 kPa)} and Int.BBG-02: 24.51 g {pale yellow oil, 19.3% yield, LC 98.2%, lot. 1403312, bp. 115 to 141.5° C. (0.15 to 0.17 kPa)} were obtained.

Synthesis of the Compound Represented by the Formula A3 from the Compound Represented by the Formula A2 (IntBBG-03 from IntBBG-02)

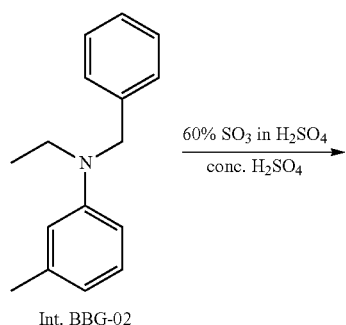

Int. BBG-02

Int BBG-02: 30.0 g (133.1 mmol, LC 98.5%, lot. 1403311) was charged to 500 mL eggplant flask, and was diluted with concentrated sulfuric acid: 132 mL, under ice-cooling (Dissolution heat was large.). Under ice-cooling, 60% fuming sulfuric acid: 20.0 mL (292.9 mmol) was dropped to this solution for 15 minutes (Reaction heat was large.). After completion of the dropping, the ice bath was removed, and the mixture was stirred for 6 hours in an oil bath at a bath temperature: 100° C.

After confirming the completion of the reaction by HPLC, the reaction solution was ice-cooled (5° C.) and was poured into ice: 900 g. Under ice-cooling, 48% NaoH aq. was cautiously added to the obtained mixture, and adjusted to pH 5 (internal temperature: 55° C. or less, pH meter was used. Reaction heat was large.) The obtained suspension was washed with AcOEt: 300 mL, and the aqueous layer was concentrated under reduced pressure (bath heat: 45 to 55° C.). At the time of concentration, toluene: 1 L×2 times and methanol: 1 L×1 time azeotropy was performed to remove water.

Methanol: 1 L was added to the obtained concentrated residue, insoluble matters were filtered off, the filtrate was concentrated under reduced pressure and dried, and a crude material of Int.BBG-03: 43.2 g (white amorphous powder, 106.2% yield, LC 72.8%, isomer 17.6%, lot. 140409) was obtained.

The crude material passed through silica gel column (N60 silica gel, acetone/water=100: 1), was gradually colored purple after repeated concentration and purification, and a slightly degradation was observed (dissolved in acetone, IPA, MeOH and the like, and concentration was performed). This crude material (light purple amorphous powder, LC 70.6%, isomer 17.8%, lot. 140409) was used as it is for the next step.

Consideration of Crystallization

Since Int.BBG-03 did not have high purification efficiency, consideration for improvement of the purification efficiency was made. By the way, it is known that Ca and Ba salts are inorganic salts but low in water solubility. Further, it was thought that salts with divalent ions would be easy to get the properties difference between the isomers, and consideration was made whether crystals of which water solubility were reduced were obtained by adding several bases including Ca. As a result of attempts to crystalize by using various bases, it was found that salt having reduced water solubility can be obtained by Cs salification of Int.BBG-03. It was also found that the ratio of isomers was improved at the Cs salification stage (isomers: 17.6%→1.1%).

Optimization of the Cs salification: $H_2O$ (substrate×35 w/v), $Cs_2CO_3$ (4.8 eq), yield 35%

When reducing $H_2O$ (substrate×15 w/v) for the purpose of improving the yield, recovery rate was increased (77%), but isomers were not removed at all.

Consideration of crystallization of Cs salt

MeOH/IPA=1/10 (×35 v/w)·recovery rate: 81%, isomers: 1.1→0.5%

$H_2O$ suspension (×5 v/w) ... recovery rate: 50%, isomers: 17.6→3.3%

$H_2O$ suspension (×2.5 v/w) ... recovery rate: 81%, isomers: 3.3→0.3%

It was found that the Cs salification of Int.BBG-03 efficiently prevent a situation in which the isomers are mixed. In the above example, a mixture of cesium carbonate and water was made to act on Int.BBG-03, but an appropriately prepared cesium salt may be reacted with Int.BBG-03 to obtain a cesium salt of Int.BBG-03.

Cs Salification of Int.BBG-03 and Purification of Int.BBG-03-Cs

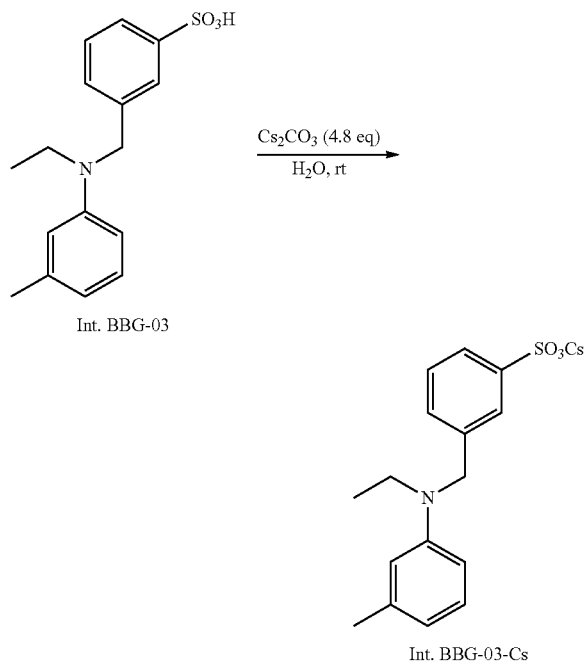

Int. BBG-03

Int. BBG-03-Cs

A crude material of Int.BBG-03: 118.9 g (389.33 mmol, LC 67.1%, isomers 20.2%, lot. 140519 and LC 70.6%, isomers 17.8%, lot. 140409), water: 4.1 L (substrate weight× 35 w/v), and $Cs_2CO_3$: 608.9 g (1.869 mol) were charged to 5 L Erlenmeyer flask, ultrasonic agitation, warming (40° C.) to make it a uniform black solution, and then seed crystal (about 50 mg) was added, left to stand for 2 hours, and cooled.

Since crystal precipitation was not observed, seed crystal (about 50 mg) was further added, and the mixture was ice-cooled and allowed to stand overnight (11 hours).

The precipitated solid (fluffy) was ice-cooled, filtered at internal temperature: 5 to 7° C., and dried under reduced pressure to obtain crude material of Int.BBG-03-Cs: 90.4 g (white solid, 53.1% yield, LC 92.5%, isomers 6.4%, lot. 1400519-crude). (*Since the solid was easily dissolved, washing was hardly performed at the time of filtering the solid.)

Water: 225 mL was added to the crude material of Int.BBG-03-Cs: 90.4 g (LC 92.5%, isomers 6.4%), and the mixture was stirred at 75 to 80° C. for 30 minutes (almost complete dissolution), and cooled to room temperature (18° C.). Seed crystal was added, and the mixture was stirred for 30 minutes.

No crystal precipitation was observed. Then, the mixture was cooled in an ice bath, and solid precipitated. The mixture was further stirred for 1.5 hours under ice-cooling, filtered, washed with water: 27 mL (×0.3 v/w), dried under reduced pressure to obtain Int.BBG-03-Cs: 68.1 g (white solid, 75.6% recovery rate, LC 95.8%, isomers 1.7%, lot. 140519-1).

A crystallization was performed by using the obtained Int.BBG-03-Cs: 68.1 g (LC 95.8%, isomers 1.7%) in the same manner as described above to obtain Int.BBG-03-Cs: 54.2 g (white solid, 79.7% recovery rate, LC 95.6%, isomers 0.41%, lot. 140519-2).

Synthesis of the Compound Represented by the Formula A4 from the Compound Represented by the Formula A3 (IntBBG-04 from IntBBG-03)

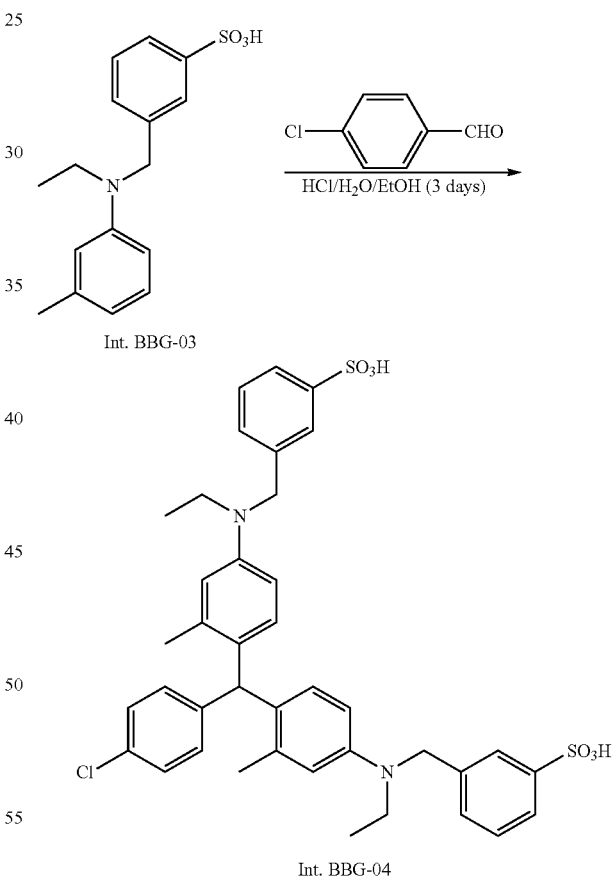

Int. BBG-03

Int. BBG-04

The crude material of Int BBG-03: 10.0 g (32.74 mmol, LC 70.6%, isomers 17.8%, lot. 140409), 4-chlorobenzaldehyde: 2.30 g (16.37 mmol), EtOH: 60 mL, and water: 180 mL were added in 500 mL eggplant flask, pH was adjusted to 0.7 by using concentrated hydrochloric acid. The reaction solution was stirred for 69 hours at a bath temperature: 120° C. In this step, it was extremely desirable to add alcohol such as ethanol to the solvent.

After confirming the reaction by HPLC (SM:TM=1:11), the reaction solution was cooled to room temperature, and pH was adjusted to 1 by using 1M NaOH aq. After adjusting pH, the reaction solution was warmed to bath temperature: 60° C., precipitate was filtered at 60° C. and washed with water to obtain crude material of Int.BBG-04: 3.48 g (white solid, 28.9% yield, LC 89.0%, isomers 4.4%).

EtOH/H$_2$O=1/3 mixture: 35 mL was added to the resulting crude material of Int.BBG-04: 3.48 g, and the suspension was stirred at bath temperature: 60° C. for 1 hour. The solid was filtered at 60° C. and washed with water, and Int.BBG-04: 3.34 g (white solid, 27.8% yield, LC 89.2%, isomers 5.5%) was obtained.

After adding EtOH/H$_2$O=1/3 mixture: 35 mL to the resulting crude material of Int.BBG-04: 3.34 g, pH was adjusted to 1 by using 1M HCl aq. After stirring the suspension at bath temperature: 60° C. for 1 hour, the solid was filtered at 60° C. and washed with water, and Int.BBG-04: 3.31 g (white solid, 27.5% yield, LC 93.5%, isomers 4.5%) was obtained.

EtOH: 35 mL was added to the resulting crude material of Int.BBG-04: 3.31 g, and the suspension was stirred at bath temperature: 60° C. for 1 hour. The solid was filtered at 60° C. and washed with EtOH, and Int.BBG-04: 3.24 g (white solid, 27.0% yield, LC 93.3%, isomers 4.5%, lot. 140425) was obtained.

In this step, the yield was extremely improved by diluting with water, cooling, and then filtering.

Synthesis of the Compound Represented by the Formula A5 from the Compound Represented by the Formula A4 (IntBBG-05 from IntBBG-04)

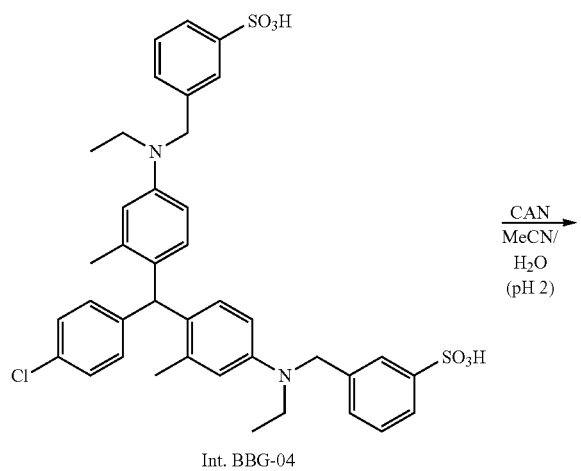

Int. BBG-04

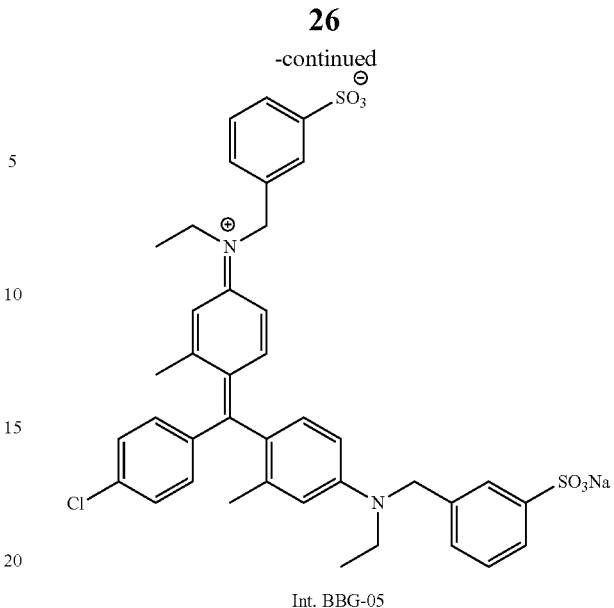

Int. BBG-05

Int BBG-04: 2.0 g (2.727 mmol, LC 93.3%, isomers 4.5%, lot. 140425), MeCN: 20 mL, and HCl/KCl aqueous buffer solution (pH 1.87): 10 mL were added in 100 mL eggplant flask, HCl/KCl aqueous buffer solution (pH 1.87) of ammonium hexanitratocerate (III) (CAN): 3.88 g (7.09 mmol) was added for 5 minutes at room temperature, and stirring was performed for 1 hour at room temperature.

After confirming the reaction by HPLC, the reaction solution was added to saturated Na$_2$SO$_4$ aqueous solution: 200 mL and n-BuOH: 200 mL, and extracted. After separating organic layer, aqueous layer was extracted by the n-BuOH: 100 mL, and organic layer was separated. The obtained organic layer was dried by Na$_2$SO$_4$, and concentrated under reduced pressure (bath temperature: 40 to 45° C.).

The resulting concentrated residue: 2.82 g was purified by silica gel column chromatography (coated with N60 silica gel: 60 g, MeOH/CHCl$_3$=1/9→2/8→3/7→4/6, and N60 silica gel: 9 g and charged), and Int.BBG-05: 1.10 g {dark green solid, 53.5% yield, LC 97.2% (254 nm), LC 98.8% (600 nm), isomers: peak not separated, lot. 140507-1} and Int.BBG-05: 0.5 g {dark green solid, 24.3% yield, LC 81.0% (254 nm), LC 91.9% (600 nm), isomers: peak not separated, lot. 140507-2} were obtained.

Synthesis of the Compound Represented by the Formula A6 from the Compound Represented by the Formula A5 (IntBBG-06 from IntBBG-05)

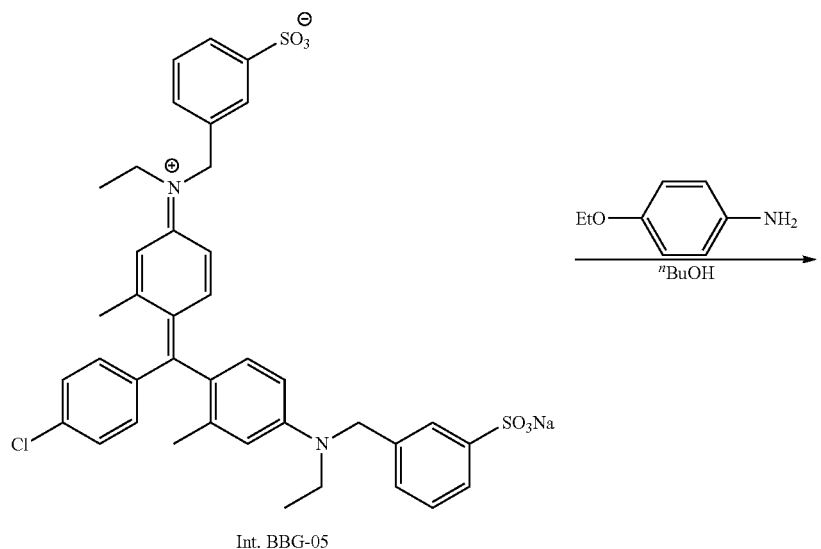

Int. BBG-05

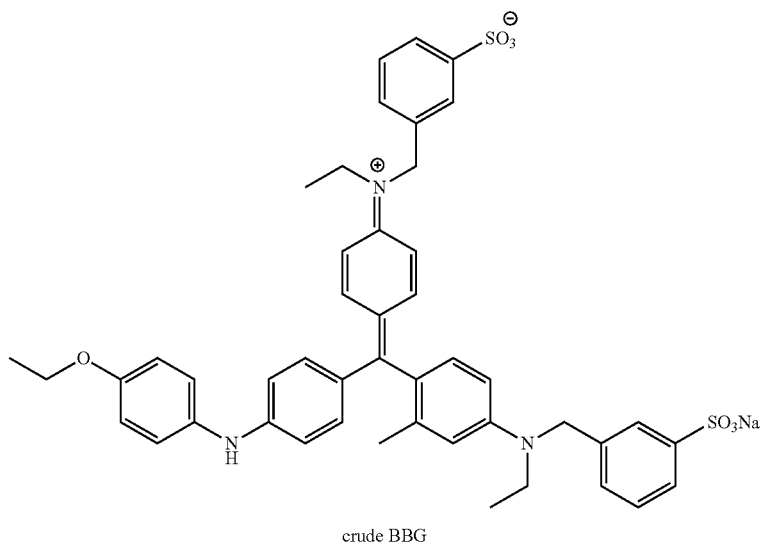

crude BBG

Int.BBG-05: 100 mg (0.1327 mmol, LC 98.8%, isomers: peak not separated, lot. 140507-1), p-phenetidine: 19.1 mg (0.1394 mmol), n-BuOH: 1 mL were added in a test tube with a screw cap at room temperature, and stirred for 15 hours at bath temperature: 105° C. Since the charge stock was remained by TLC, the reaction solution was returned to room temperature, p-phenetidine: 3.6 mg (0.02654 mmol) was added to the reaction solution, and then stirring was performed for 2 hours at bath temperature: 105° C. Since the charge stock was remained by TLC, the reaction solution was returned to room temperature again, p-phenetidine: 18.2 mg (0.1327 mmol) was added to the reaction solution, and then stirring was performed for 2 hours at bath temperature: 105° C.

After confirming the reaction by TLC, 0.5 M HCl aq.: 10 mL was added to the reaction solution, and the reaction solution was concentrated under reduced pressure (transferred by IPA, bath temperature: 40 to 45° C.). 0.5 M HCl aq.: 10 mL was added in an eggplant flask, ultrasonic processing and solid separation with a spatula were performed, and the solid was filtered and washed with 0.5 M HCl aq. The obtained solid was dried under reduced pressure, and crude BBG: 81.1 mg (deep red purple solid, 72.0% yield, LC 87.7% (600 nm), lot. 140514) was obtained.

Example 2

Synthesis of the Compound Represented by the Formula B2 from the Compound Represented by the Formula B1 (IntBBG-025-1 from IntBBG-01)

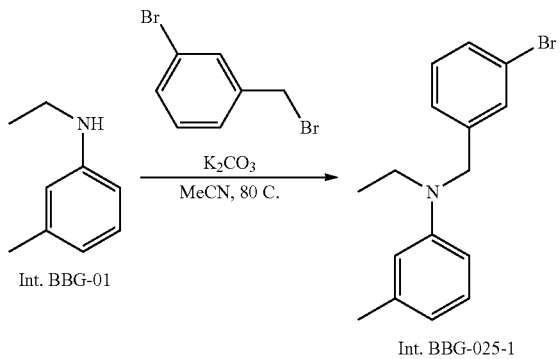

Int. BBG-01

Int. BBG-025-1

Int BBG-01: 13.36 g (98.55 mmol, TC1), $K_2CO_3$: 20.42 g (147.8 mmol, wako), MeCN: 98 mL were charged to 300 mL eggplant flask, m-bromo benzyl bromide: 24.63 g (98.55 mmol, wako) was added at room temperature, and stirring was carried out for 1 hour at room temperature.

After confirming the reaction by TLC, insoluble matter was filtered off and the filtrate was concentrated under reduced pressure. Water: 200 mL and AcOEt: 200 mL were added to the obtained concentrated residue and organic layer was separated by a separating operation. After washing the obtained organic layer with brine: 100 mL, dried with $Na_2SO_4$, and concentrated under reduced pressure (bath temperature: 35 to 45° C.).

The obtained concentrated residue (30.19 g) was purified by silica gel column chromatography (N60 silica gel 90 g, 20% AcOEt/Heptane), and Int BBG-025-1: 29.40 g (pale yellow oil, 97.8% yield, lot. 140523) was obtained.

Synthesis of the Compound Represented by the Formula B2-1 from the Compound Represented by the Formula B2 (IntBBG-025-2 from IntBBG-025-1)

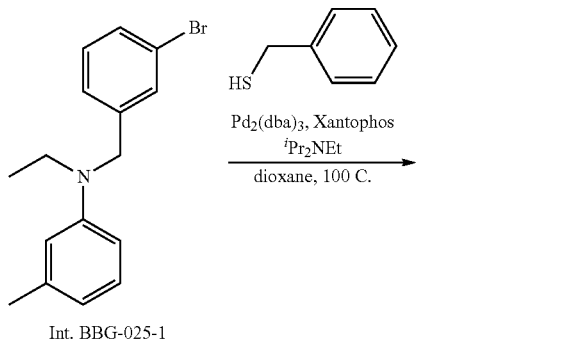

Int. BBG-025-1

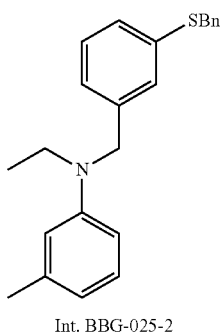

Int. BBG-025-2

Under Ar stream, Int BBG-025-1: 10.4 g (34.18 mmol, LC 96.8%, lot. 140523), DIPEA: 11.8 mL (68.36 mmol), and dehydrated dioxane: 100 mL were charged to 300 mL Kolben, and Ar bubbling was carried out for 10 minutes at room temperature. Benzyl mercaptan: 4.21 mL (35.89 mmol), Xantophos: 989 mg (1.709 mmol), $Pd_2(dba)3$: 782 mg (0.8545 mmol) were added sequentially to the reaction solution, and stirring was carried out for 1 hour at internal temperature: 95° C.

After confirming the reaction by HPLC, the reaction solution was returned to room temperature, AcOEt: 200 mL was added thereto, and insoluble matters were dissolved partially. The reaction solution was filtered by a mix pad of celite/silica gel=50 g/50 g and washed with AcOEt, and the filtrate was concentrated under reduced pressure (bath temperature: 35 to 45° C.).

The obtained concentrated residue 17.38 g was purified by silica gel column chromatography (N60 flash silica gel 200 g, 1% AcOEt/Heptane), and Int BBG-025-2: 12.65 g (pale yellow oil, 106.5% yield, LC 96.8%, lot. 140527) was obtained.

Synthesis of the Compound Represented by the Formula B3 from the Compound Represented by the Formula B2-1 (IntBBG-025-3 from IntBBG-025-2)

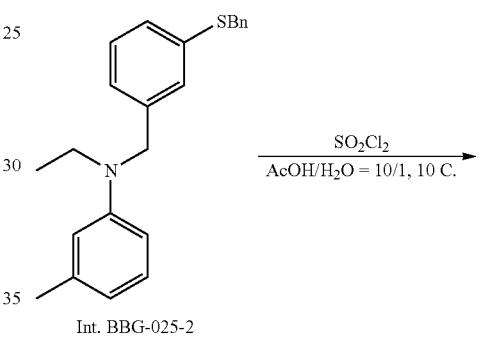

Int. BBG-025-2

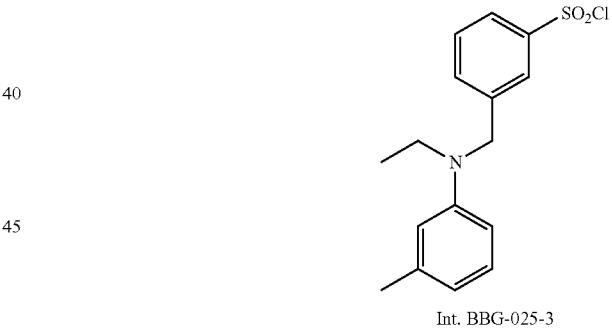

Int. BBG-025-3

Int BBG-025-2: 408 mg (1.174 mmol, LC 96.7%, lot. 140527) and AcOH: 4 mL were charged to a test tube with screw cap, and the mixture was cooled to 10° C. AcOH: 1.5 mL solution of $SO_2Cl_2$: 0.38 mL (4.696 mmol) was dropped to the reaction solution for 5 minutes at 10° C., and stirring was carried out for 30 minutes at the same temperature. It was important to add $SO_2Cl_2$ slowly as the AcOH solution.

After confirming the reaction by HPLC, the reaction solution was poured into ice-cooled sat. $NaHCO_3$ aq.: 100 mL and extracted by AcOEt: 100 mL. The obtained organic layer was washed with sat. $NaHCO_3$ aq.: 50 mL, dried with $Na_2SO_4$, and concentrated under reduced pressure (bath temperature: 35 to 45° C.), and a crude material of Int.BBG-025-3: 323 mg (pale yellow oil, 85.0% yield, LC 91.0%, lot. 140528) was obtained.

Synthesis of the Compound Represented by the Formula B4 from the Compound Represented by the Formula B3 (IntBBG-03-Na from IntBBG-025-3)

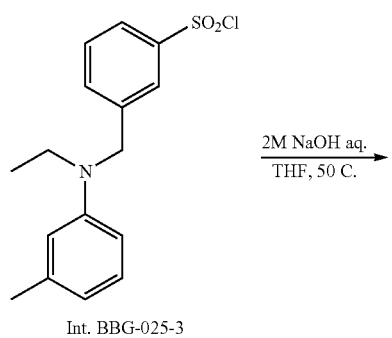

Int. BBG-025-3

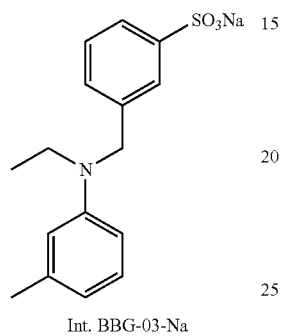

Int. BBG-03-Na

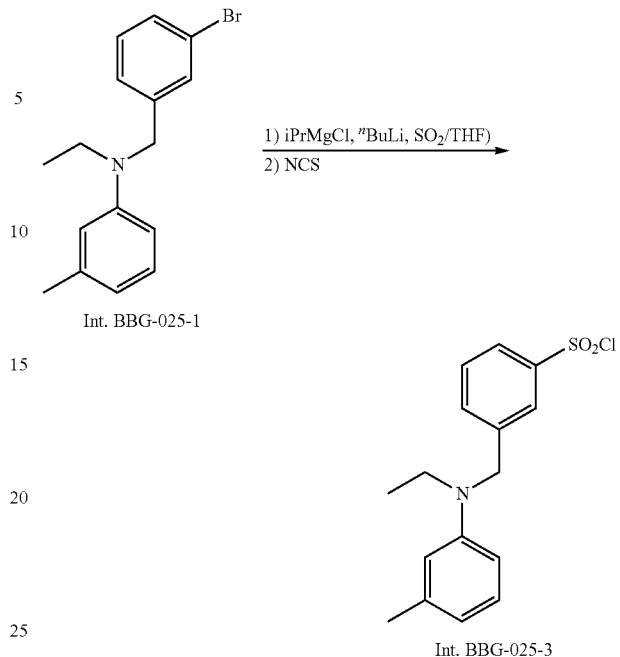

Int.BBG-025-3: 301 mg (0.9387 mmol, LC 91.0%, lot. 140528), THF: 3 mL, and 2M NaOH aq.: 0.94 mL (1.878 mmol) were charged to 10 mL eggplant flask, and stirring was carried out for 30 minutes at 50° C.

After confirming the reaction by HPLC, the reaction solution was concentrated under reduced pressure (bath temperature: 45 to 50° C.). After azeotrope of the concentrated residue with toluene: 10 mL×2 times and methanol: 10 mL×1 time, methanol 10 mL was added thereto, and insoluble matters were filtered off. Before concentration to dryness of the obtained filtrate, MeOH/IPA crystallization was carried out (dissolving in MeOH, concentrating partially, adding IPA, and concentrating partially were repeated to replace with IPA, and then ultrasonic waves were applied to crush the solid, stirring was carried out for 30 minutes at 0° C., and filtered), Int.BBG-03-Na: 153.7 mg (white solid, 50.0% yield, LC 90.3%, lot. 140529-1) and a mother liquor concentrate: 204 mg (white amorphous semisolid, 66.4% yield, LC 59.6%, lot. 140529-2) were obtained.

In addition to the above, reaction was carried out in the same manner by using Int BBG-025-3: 879 mg (2.31 mmol, purity 91.6% by LC-MS, lot. 140525).

After confirming the reaction by HPLC, the reaction solution was concentrated under reduced pressure (bath temperature: 45 to 50° C.). After azeotrope of the concentrated residue with methanol: 20 mL×3 times, methanol 10 mL was added thereto, and insoluble matters were filtered off.

The obtained filtrate was concentrated under reduced pressure and dried, and a crude material of Int. BBG-03-Na: 776 mg (white solid, quant, LC 88.0%, lot. 140526) was obtained.

Example 3

Synthesis of the Compound Represented by the Formula B3 from the Compound Represented by the Formula B2 (IntBBG-025-3 from IntBBG-025-1)

Under Ar stream, i-PrMgCl (1.0 M in $Et_2O$): 1.6 mL (1.6 mmol) and THF (dehydrated): 20 mL were charged to 100 mL Kolben and cooled to −70° C. n-BuLi (1.55 M in n-hexane): 2.06 mL (3.2 mmol) was added to the reaction solution at −70° C., and stirring was carried out for 10 minutes. THF (dehydrated) 5 mL solution of Int BBG-025-2: 1.216 g (4.0 mmol, C, lot. 1740522) was dropped into the reaction solution at −70° C., and stirring was carried out for 1 hour at −60° C. Since the charge stock was remained, i-PrMgCl (1.0 M in $Et_2O$): 0.32 mL (0.32 mmol) and n-BuLi (1.55M in n-hexane): 0.41 mL (0.64 mmol) were added sequentially to the reaction solution at −60° C., and stirring was carried out for 10 minutes at −60° C.

$SO_2$ (7.7 M in THF) solution: 5.2 mL (40.0 mmol) was dropped into the reaction solution at −65° C. (internal temperature: −65° C. to −55° C.), and stirring was carried out for 1.5 hours at −60° C.

After adding NCS: 650 mg (5.76 mmol) to the reaction solution at −60° C. and stirring for 30 minutes at −20° C., temperature rose naturally, and stirring was performed for 15 hours at −20° C. to room temperature. After confirming the reaction by LC-MS, water: 100 mL and AcOEt: 100 mL were added thereto and extracted.

The obtained organic layer was washed with water: 50 mL and brine: 50 mL, dried with $Na_2SO_4$, and concentrated under reduced pressure (bath temperature: 35 to 45° C.).

The obtained concentrated residue 1.50 g was purified by silica gel column chromatography (N60 flash silica gel 60 g, AcOEt/Heptane=1/20), and Int BBG-025-3: 879 mg (pale yellow oil, 67.9% yield, purity 91.6% by LC-MS, lot. 140525) was obtained.

INDUSTRIAL APPLICABILITY

The present invention can be utilized in chemical and pharmaceutical industries.

What is claimed is:
1. A triaryl methane composition comprising at least one triaryl methane derivatives of formulas (1) to (3) and the pharmaceutically acceptable salts thereof,

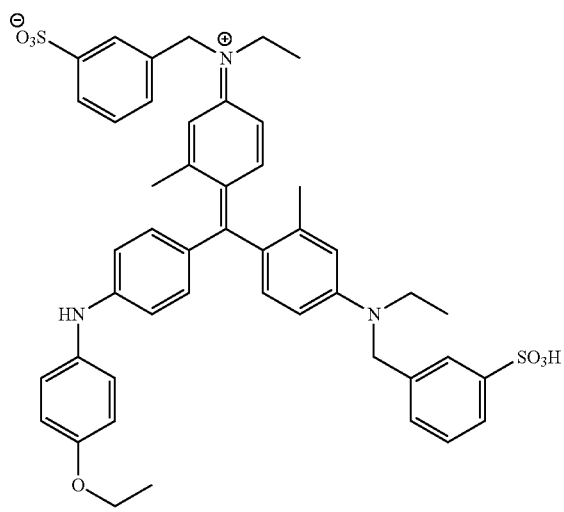

(1)

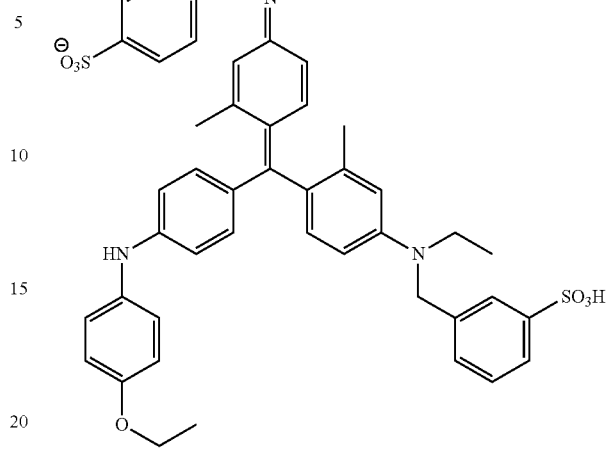

(3)

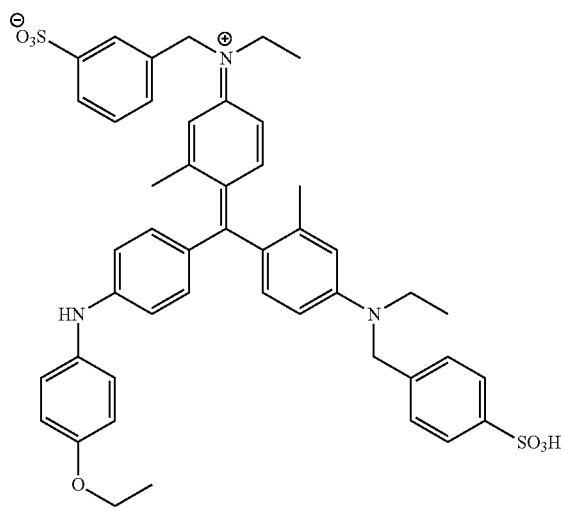

(2)

and a pharmacologically acceptable carrier
wherein the composition comprises at least 90 wt % of Brilliant Blue G (BBG) represented by the formula (1) or a pharmaceutically acceptable salt thereof.

2. A dye composition for ocular membrane dyeing used in removing an ocular membrane, comprising the triaryl methane composition of claim 1.

3. A method for removing the ocular membrane of a human patient, comprising:

(a) dyeing the ocular membrane of a patient by using a dyeing composition; and (b) peeling the ocular membrane stained by the dyeing composition, wherein the composition is the triaryl methane composition of claim 1.

\* \* \* \* \*